(12) United States Patent
Vogel et al.

(10) Patent No.: US 10,849,837 B2
(45) Date of Patent: Dec. 1, 2020

(54) SOLID ANHYDROUS COMPOSITION FOR KERATIN FIBERS

(71) Applicant: KAO GERMANY GMBH, Darmstadt (DE)

(72) Inventors: Nicole Vogel, Niedernhausen (DE); Christine Cajan, Bad Ems (DE)

(73) Assignee: KAO GERMANY GMBH, Darmstadt (DE)

( * ) Notice: Subject to any disclaimer, the term of this patent is extended or adjusted under 35 U.S.C. 154(b) by 703 days.

(21) Appl. No.: 15/470,371

(22) Filed: Mar. 27, 2017

(65) Prior Publication Data

US 2017/0196785 A1 Jul. 13, 2017

Related U.S. Application Data

(63) Continuation of application No. 13/057,109, filed as application No. PCT/EP2009/006001 on Aug. 19, 2009, now abandoned.

(30) Foreign Application Priority Data

Aug. 20, 2008 (EP) ..................... 08014761

(51) Int. Cl.

| | | |
|---|---|---|
| *A61Q 5/06* | (2006.01) | |
| *A61Q 5/12* | (2006.01) | |
| *A61K 8/34* | (2006.01) | |
| *A61K 8/36* | (2006.01) | |
| *A61K 8/02* | (2006.01) | |
| *A61K 8/35* | (2006.01) | |
| *A61K 8/39* | (2006.01) | |
| *A61K 8/81* | (2006.01) | |
| *A61K 8/891* | (2006.01) | |

(52) U.S. Cl.
CPC ............ *A61K 8/345* (2013.01); *A61K 8/0216* (2013.01); *A61K 8/34* (2013.01); *A61K 8/35* (2013.01); *A61K 8/361* (2013.01); *A61K 8/39* (2013.01); *A61K 8/8182* (2013.01); *A61K 8/891* (2013.01); *A61Q 5/06* (2013.01); *A61Q 5/065* (2013.01); *A61Q 5/12* (2013.01); *A61K 2800/262* (2013.01); *A61K 2800/30* (2013.01); *A61K 2800/31* (2013.01); *A61K 2800/432* (2013.01); *A61K 2800/52* (2013.01)

(58) Field of Classification Search
None
See application file for complete search history.

(56) References Cited

U.S. PATENT DOCUMENTS

| 4,344,446 A | 8/1982 | Ehrhardt |
|---|---|---|
| 5,284,649 A | 2/1994 | Juneja |
| 6,090,375 A | 7/2000 | Rechelbacher |
| 6,689,728 B2 * | 2/2004 | Diez ................. C11D 13/16 510/147 |
| 7,255,869 B2 | 8/2007 | Uchida et al. |
| 2002/0076424 A1 | 6/2002 | Birkel |
| 2005/0039269 A1 * | 2/2005 | Smith ................. A61K 8/97 8/405 |
| 2008/0095807 A1 | 4/2008 | Zabari |

FOREIGN PATENT DOCUMENTS

| EP | 0 024 365 A | 3/1981 | |
|---|---|---|---|
| EP | 0 447 142 A | 9/1991 | |
| EP | 1 911 440 A1 | 4/2008 | |
| WO | 2006/015149 A1 | 2/2006 | |
| WO | WO-2006015149 A1 * | 2/2006 | ........... C11D 3/3707 |

OTHER PUBLICATIONS

International Search Report dated Aug. 3, 2010.

* cited by examiner

*Primary Examiner* — Jyothsna A Venkat
(74) *Attorney, Agent, or Firm* — Norris McLaughlin, P.A.

(57) ABSTRACT

Present invention is on an anhydrous solid conditioning and styling, composition for keratin fibres, especially human hair. The object of the present invention is a solid anhydrous composition for keratin fibres, especially for human hair, comprising at least one polyol liquid at 20° C. at a concentration 50% or more by weight and at least one fatty acid soap at a concentration of 5% or more by weight, all values calculated to total composition, wherein the composition is free of volatile organic solvents, especially $C_1$-$C_4$ aliphatic alcohol.

8 Claims, No Drawings

SOLID ANHYDROUS COMPOSITION FOR KERATIN FIBERS

This is a continuation patent application of U.S. Ser. No. 13/057,109 filed on Feb. 1, 2011, which is a 371 application of PCT/EP2009/006001, filed Aug. 19, 2009, which claims foreign priority benefit under 35 U.S.C. § 119 of European Application No. 08014761.4 filed Aug. 20, 2008.

Present invention is on an anhydrous solid conditioning and styling, composition for keratin fibres, especially human hair.

Solid conditioning in particular styling compositions are available on the market. Generally they are aqueous compositions and/or comprising water at certain level and additionally comprising volatile organic solvents in particular lower aliphatic alcohols and especially $C_1$ to $C_4$ aliphatic alcohols.

These compositions are not satisfactorily stable as shrinkage occurs because of evaporation of water and other volatile solvents takes place during longer storage periods even at ambient and lower temperature ranges. Solid compositions are often suitably packed in a stick-form into a holder which is necessarily air-tight. Therefore, there is a great need for improvement and especially eliminating such kind of stability problem in order to achieve long living products at the market place.

Accordingly, the first objective of the present invention is to provide a solid conditioning and especially styling composition for keratin fibres, especially human hair with improved stability.

The second object of the present invention is to provide a composition in solid form to be used for styling hair and especially for improving shine, preventing fly-away and for anti-frizzy effect.

The inventors have surprisingly found out that a solid anhydrous composition comprising at least one polyol liquid at 20° C. and at least one fatty acid soap has improved stability properties over a long storage period and improves hair shine, prevents fly-away and shows excellent anti-frizz effect.

Accordingly, the first object of the present invention is a solid anhydrous composition for keratin fibres, especially for human hair, comprising at least one polyol liquid at 20° C. at a concentration 50% or more by weight and at least one fatty acid soap at a concentration of 5% or more by weight, all values calculated to total composition, wherein the composition is free of volatile organic solvents, especially $C_1$-$C_4$ aliphatic alcohol.

Further object of the present invention is the use of a solid anhydrous conditioning composition for keratin fibres, especially for human hair, comprising at least one polyol liquid at 20° C. at a concentration greater than 50% by weight and at least one fatty acid soap at a concentration of 5% by weight and more, all values calculated to total composition, wherein the composition is free of volatile organic solvents especially $C_1$-$C_4$ aliphatic alcohol for conditioning and styling keratin fibres, especially human hair and especially for improving hair shine and preventing fly-away.

Still further object of the present invention is a process for conditioning and styling keratin fibres, especially human hair, wherein a composition comprising at least one polyol liquid at 20° C. at a concentration greater than 50% by weight and at least one fatty acid soap at a concentration of 5% by weight or more, all values calculated to total composition, wherein the composition is free of volatile organic solvents especially $C_1$-$C_4$ aliphatic alcohol is applied onto wet or dry keratin fibres, especially human hair and not rinsed off.

Composition of the present invention comprise at least one polyol liquid at 20° at a concentration of at least 50% by weight calculated to total composition. Concentration of at least one polyol is preferably at least 60% and more preferably at least 70% by weight, calculated to total composition.

With the term polyol it is meant any compound, preferably aliphatic compounds, having 2 or more hydroxyl groups in its molecule.

With the term anhydrous it is meant that compositions do not comprise any water and other volatile solvents as added. However it is possible that water and other volatile organic solvents are incorporated into the compositions at minor concentrations due to use of raw materials which comprise such compounds.

The term liquid means that polyol compound is free flowing and can comprise unmelted parts dispersed in it.

Suitable polyols are according to the general formula

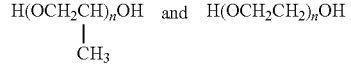

wherein n is a number between 1 and 20, preferably between 1 and 16 and more preferably between 1 and 13 and most preferably between 1 and 10.

Examples to (poly)propylene glycols suitable are propylene glycol, PPG-3, PPG-7, PPG-9, PPG-12, PPG-13, PPG-15, PPG-16, PPG-17, and PPG-20. Preferred are propylene glycol, PPG-3, PPG-7, PPG-9, PPG-12, PPG-13, PPG-15, and PPG-16. More preferred are propylene glycol, PPG-3, PPG-7, PPG-9, PPG-12, and PPG-13. Most preferred are propylene glycol, PPG-3, PPG-7, and PPG-9. In particular, propylene glycol is found to be excellently suitable.

Examples to (poly)ethyleneglycols are PEG-4, PEG-6, PEG-7, PEG-8, PEG-9, PEG-10, PEG-12, PEG-14, PEG-16, PEG-18, and PEG-20. Preferred are PEG-4, PEG-6, PEG-7, PEG-8, PEG-9, PEG-10, PEG-12, PEG-14, and PEG-16. More preferred are PEG-4, PEG-6, PEG-7, PEG-8, PEG-9, PEG-10, and PEG-12. Most preferred are PEG-4, PEG-6, PEG-7, PEG-8, PEG-9, and PEG-10. In particular, PEG-8 is found to be excellently suitable.

In a preferred embodiment of the present invention, composition comprises at least one (poly)propylene glycol according to the general formula give above and at least one (poly)ethyleneglycol at a (poly)propylene glycol to (poly)ethyleneglycol weight ratio of 10:1 to 1:10, preferably 5:1 to 1:5 and more preferably 3:1 to 1:3 and most preferably 1:1.

Composition of the present invention comprise at least one fatty acid soap at a concentration of 5% by weight or more, preferably 5 to 20%, more preferably 5 to 15% and most preferably 7.5 to 12.5% by weight calculated to total composition.

Preferred fatty acid soap is sodium soap and most preferred is sodium stearate.

Composition of present invention is preferably semi-transparent and more preferably transparent. Transparency is judged macroscopically at a composition thickness of approximately 1 cm either in a transparent vessel or as it is.

Composition comprises preferably at least one film forming—styling polymer soluble in the composition. Preferred are non-ionic polymers.

With the term solubility it is meant that at the concentration polymer used in the composition it is dissolved without leaving any remains at ambient temperature which is approximately 20° C.

Non-limiting examples to suitable non-ionic polymers are vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 64 from BASF AG.

Natural non-ionic polymers are as well suitable for the composition of the present invention. Those are such as cellulose, chitosan, guar gum and their derivatives.

Film forming styling polymers are comprised in the compositions of the present invention at a concentration of 0.1 to 10%, preferably 0.25 to 7.5% and more preferably 0.5 to 5% by weight calculated to total composition.

Composition can comprise silicone compounds. It is the preferred embodiment that the compositions comprise at least one silicone compound. The silicone compound is preferably soluble in the remaining of the composition. Suitable ones are dimethicone, dimethiconol, cyclic silicones, arylated silicone and amino silicones. Preferably, useful silicones are non volatile silicones, however volatile ones can also be comprised at concentration that does not cause any instability. Another condition is that the silicone used in the compositions must be full soluble and/or miscible with the other parts of the composition. Nonlimition examples are dimethicones as available from Dow Corning with various viscosities, cyclosiloxanes such as cyclopantasilocane, cyclotetrasiloxane and cyclotrisiloxane, arylated silicones such as phenyl trimethicone, phenyl methicone, trimethyl pentaphenyl trisiloxane, aminated silicones such as quaternium-80, amodimethicone and polysilicone-9. With the term aminated silicone it is meant that silicone compounds comprising at least one secondary, tertiary or quaternary amino group. Concentration of any of the silicone compounds is in the range of 0.01 to 5%, preferably 0.1 to 4% and more preferably 0.25 to 2.5% by weight calculated to total composition.

In a preferred form of the invention, composition comprises at least one fatty acid fatty alcohol ester according to general formula

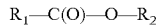

$$R_1-C(O)-O-R_2$$

wherein $R_1$ is straight or branched, saturated or unsaturated with 8 to 22 C atoms, preferably 12 to 18 C atoms and $R_2$ is straight or branched, saturated or unsaturated 1 to 6 C atoms, preferably 2 to 4 C atoms.

Non-limiting suitable examples are isopropyl palmitate, ethyl palmitate, butyl palmitate, isobutyl palmitate, methyl palmitate, hexyl palmitate, isohexyl palmitate, methyl myristate, isopropyl myristate, butyl myristate, ethyl myristate, isobutyl myristate, isopropyl laurate, ethyl laurate, butyl laurate, isobutyl laurate, methyl laurate, hexyl laurate, isohexyl laurate, isopropyl stearate, ethyl stearate, butyl stearate, isobutyl stearate, methyl stearate, hexyl stearate and isohexyl stearate. Fatty acid fatty alcohol ester is comprised in the compositions at a concentration of 0.01 to 2%, preferably 0.1 to 1% by weight calculated to total composition.

Composition of the present invention may comprise surfactants of anionic, non-ionic or amphoteric character. Non-ionic surfactants are the most preferred ones. Preferred non-ionic surfactants are fatty alcohol ethoxylates such as Ceteareth-20, Ceteareth-30, Ceteareth-40, Ceteth-20, Ceteth-30, Ceteth-40, Steareth-20, Steareth-25 and Steareth-20.

Further preferred non-ionic surfactants are ethoxylated trigylcerides such as PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil, PEG-100 castor oil, PEG-200 castor oil.

Total surfactant concentration of the compositions other than fatty acid soap is in the range of 0.1 to 10%, preferably 0.25 to 7.5% by weight calculated to total composition.

Composition of the present invention preferably comprises at least one UV filter. Concentration of UV filter is in the range of 0.1 to 5%, preferably 0.25 to 4% by weight calculated to total composition. Non-limiting suitable examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzophenone or the sodium salt thereof, 2-hydroxy-4-octyloxybenzophenone, 2-hydroxy-4-methoxy-4'-methylbenzophenone, 3-benzyl-idenecamphor, 3-(4'-sulfo)-benzyl-idenebornane-2-one and the salts thereof and/or 3-(4'-methyl benzylidene)-DL-campher.

Direct dyes of anionic, cationic, and/or nonionic character can be comprised in the compositions of the present invention. Preferred direct dyes are of cationic direct dyes for hair colouring purposes. In the case of product colouring anionic dyes are more preferred. Concentration is in the range of 0.0001 to 1% by weight, calculated to total composition.

In the selection of direct dyes, compatibility of the dye with the rest of the composition must be taken into account.

Suitable cationic direct dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and mixtures thereof Any anionic dye is in principal suitable for the compositions, especially for giving compositions an attractive colour. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Green 3, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and mixtures thereof.

Neutral dyes, so called nitro dyes for hair colouring purposes can also be contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and mixtures thereof.

Hardness of the solid conditioning compositions of the present invention can be characterised with a penetration value. The penetration value can be determined with a commercially available penetrometer (SUR Berlin PNR 10) at 20° C. In the preferred embodiment of the present invention, composition has a penetration value between 1 and 30 mm, preferably between 2 and 20 mm, more preferably between 5 and 20 mm determined at 20° C.

Composition of the present invention further comprises ingredients common to the any cosmetic compositions, such as fragrance, preservatives, acids and/or basis for adjusting pH, etc.

The following examples are used to demonstrate the invention but not to limit.

EXAMPLE 1

|  | % by weight |
| --- | --- |
| Propylene glycol | 89.5 |
| Sodium stearate | 10 |
| Fragrance | 0.5 |

The composition was prepared by dissolving sodium stearate in propylene glycol with the use of heat. After cooling at approximately room temperature fragrance was added and further mixed to homogeneity. The resulting solid composition had a penetration depth of 6.7 mm measured at 20° C. with above mentioned equipment. The resulting composition is transparent and stable over 6 months in a temperature range of 5 to 40° C. (isotherm storage).

The composition was applied on dry hair and was observed that hair became more shine, easily stylable and had less flay-aways.

EXAMPLE 2

|  | % by weight |
| --- | --- |
| Propylene glycol | 45 |
| PEG-8 | 45 |
| Sodium stearate | 9.5 |
| Fragrance | 0.5 |

The composition was prepared in the same way as in example 1. The resulting composition was transparent and was stable over 6 months in a temperature range of 5 to 40° C. (isotherm storage).

The composition was applied on dry hair and was observed that hair became more shine and fly-aways were reduced dramatically, at the same time hair was styled very easily.

EXAMPLE 3

|  | % by weight |
| --- | --- |
| Propylene glycol | 47 |
| PEG-8 | 40 |
| Sodium stearate | 8.5 |
| Luviskol VA 64 | 4 |
| Fragrance | 0.5 |

The composition was prepared by dissolving sodium stearate and Luviskol VA 64 in propylene glycol and PEG-8 mixture in presence of heat. After cooling at approximately room temperature fragrance was added and further mixed to homogeneity. The resulting composition was transparent and was stable over 6 months in a temperature range of 5 to 40° C. (isotherm storage).

The composition was applied on wet hair and was observed that hair was easily styled and became more shine, less fly-aways.

EXAMPLE 4

|  | % by weight |
| --- | --- |
| Propylene glycol | 45 |
| PEG-8 | 42 |
| Sodium stearate | 9.5 |
| Luviskol VA 64 | 2.5 |
| Benzophenone-3 | 0.5 |
| Fragrance | 0.5 |

The composition was prepared by dissolving sodium stearate and Luviskol VA 64 in propylene glycol and PEG-8 mixture in presence of heat and combining it with Benzophenone-3. The resulting composition was transparent and was stable over 6 months in a temperature range of 5 to 40° C. (isotherm storage).

The composition was applied on wet hair and was observed that hair was easily styled and became more shine, less fly-aways. The composition provided particular UV protection.

EXAMPLE 5

|  | % by weight |
| --- | --- |
| Propylene glycol | 45 |
| PEG-8 | 42 |
| Sodium stearate | 11.5 |
| Isoproypl palmitate | 0.5 |
| Benzophenone-3 | 0.5 |
| Fragrance | 0.5 |

The composition was prepared by dissolving sodium stearate in propylene glycol and PEG-8 mixture in presence of heat and remaining ingredients are combined subsequently. Fragrance was added after cooling the composition down to below 40° C. The resulting composition was transparent and was stable over 6 months in a temperature range of 5 to 40° C. (isotherm storage).

The composition was applied on wet hair and was observed that hair was easily styled and became more shine, less fly-aways. The composition provided particular UV protection.

EXAMPLE 6

|  | % by weight |
| --- | --- |
| Propylene glycol | 41 |
| PEG-8 | 41 |
| Sodium stearate | 11.5 |
| Luviskol VA 64 | 5 |
| Phenyl methicone | 0.5 |
| Benzophenone-3 | 0.5 |
| Fragrance | 0.5 |

The composition was prepared in the same way as in Example 4. The resulting composition was transparent and was stable over 6 months in a temperature range of 5 to 40° C. (isotherm storage).

The composition was applied on wet hair and was observed that hair was easily styled and became more shine, less fly-aways and also provided UV protection.

EXAMPLE 7

|  | % by weight |
| --- | --- |
| Propylene glycol | 43 |
| PEG-8 | 43 |
| Sodium stearate | 7.5 |
| Luviskol VA 64 | 5 |
| Isopropyl palmitate | 0.5 |
| Basic red 51 | 0.1 |
| Benzophenone-3 | 0.5 |
| Fragrance | 0.4 |

The composition was prepared in the same way as in example 6. The resulting composition was transparent and was stable over 6 months in a temperature range of 5 to 40° C. (isotherm storage).

The composition was applied on wet hair and was observed that hair was easily styled and had red shimmery shine.

EXAMPLE 8

|  | % by weight |
| --- | --- |
| Propylene glycol | 46 |
| PEG-8 | 40 |
| Sodium stearate | 7.5 |
| Luviskol VA 64 | 5 |
| Polysilicone-9 | 0.5 |
| Basic blue 99 | 0.01 |
| Benzophenone-3 | 0.5 |
| Fragrance | 0.49 |

The composition was prepared in the same way as in example 7. The resulting composition was transparent and was stable over 6 months in a temperature range of 5 to 40° C. (isotherm storage).

The composition was applied on wet hair and was observed that hair was easily styled and had less fly-away. Excellent anti-yellowing effect was observed on gray hair.

EXAMPLE 9

|  | % by weight |
| --- | --- |
| Propylene glycol | 43 |
| PEG-8 | 43 |
| Sodium stearate | 7.5 |
| Luviskol VA 64 | 5 |
| Dimethicone | 0.5 |
| Benzophenone-3 | 0.5 |
| Basic red 51 | 0.05 |
| Basic yellow 87 | 0.02 |
| Basic orange | 0.02 |
| Fragrance | 0.41 |

The composition was prepared in the same way as in example 7. The resulting composition was transparent and was stable over 6 months in a temperature range of 5 to 40° C. (isotherm storage).

The composition was applied on wet hair and was observed that hair was easily styled, had excellent blond shine and had less fly-aways.

EXAMPLE 10

|  | % by weight |
| --- | --- |
| Propylene glycol | 42 |
| PEG-8 | 42 |
| Sodium stearate | 9.5 |
| Luviskol VA 64 | 5 |
| Trimethyl pentaphenyl trisiloxane | 0.5 |
| Benzophenone-3 | 0.5 |
| Acid red 52 | 0.001 |
| CI 47005 | 0.002 |
| Fragrance | 0.497 |

The composition was prepared in the same way as in example 7. The resulting composition was transparent and was stable over 6 months in a temperature range of 5 to 40° C. (isotherm storage). The composition has a stable red-orange colour.

The composition was applied on wet hair and was observed that hair was easily styled and had less fly-aways.

We claim:

1. A method for conditioning and styling human hair, the method comprising:
   providing a solid anhydrous composition comprising:
   at least one polyol liquid at 20° C. selected from compounds according to general formulas:

$$H(OCH_2CH)_nOH \quad \text{and} \quad H(OCH_2CH_2)_nOH$$
   $$\hspace{1.2cm} | $$
   $$\hspace{1.2cm} CH_3$$

wherein n is a number between 1 and 20 at a concentration of at least 70% by weight; and
   fatty acid sodium soap at a concentration of 5% to 20%, all values are calculated to a total of the solid anhydrous composition,
   wherein the solid anhydrous composition is free of volatile organic solvents comprising $C_1$-$C_4$ aliphatic alcohol.

2. The method according to claim 1, wherein the solid anhydrous composition further comprises:
   at least one film forming styling polymer that is soluble in the solid anhydrous composition at 20° C. and present at a concentration of 0.1 to 10% by weight calculated to the total of the solid anhydrous composition.

3. The method according to claim 1, wherein the solid anhydrous composition further comprises:
   at least one silicone compound.

4. The method according to claim 1, wherein the solid anhydrous composition further comprises:
   at least one fatty acid fatty alcohol ester in accordance with the following general formula $$R_1\text{—}C(O)\text{—}O\text{—}R_2$$

wherein $R_1$ is straight or branched, saturated or unsaturated with 8 to 22 carbon atoms and $R_2$ is straight or branched, saturated or unsaturated 1 to 6 carbon atoms.

5. The method according to claim 1, wherein the solid anhydrous composition further comprises:
   at least one surfactant selected from non-ionic surfactant, anionic surfactant, and amphoteric surfactant.

6. The method according to claim 5, wherein the at least one surfactant is one selected from a non-ionic surfactant and an anionic surfactant.

7. The method according to claim 1, wherein the solid anhydrous composition further comprises:
   at least one UV filter.

8. The method according to claim 1, wherein the solid anhydrous composition further comprises:
   at least one direct dye.

* * * * *